United States Patent [19]

Abou-Gharbia

[11] Patent Number: 5,036,070
[45] Date of Patent: Jul. 30, 1991

[54] POLYCYCLIC PHENALKYL AMINES AS PSYCHOTROPIC AGENTS

[75] Inventor: Magid A. Abou-Gharbia, Glen Mills, Pa.

[73] Assignee: American Home Products Corporation, New York, N.Y.

[21] Appl. No.: 537,551

[22] Filed: Jun. 13, 1990

[51] Int. Cl.$^5$ .................. A61K 31/495; A61K 31/36; C07D 401/04; C07D 319/20
[52] U.S. Cl. ...................................... 514/252; 514/456; 544/238; 544/295; 544/357; 544/360; 544/369; 549/366
[58] Field of Search ............... 544/238, 295, 357, 360, 544/396; 549/366; 514/252, 456

[56] References Cited

U.S. PATENT DOCUMENTS

| | | | |
|---|---|---|---|
| 4,339,580 | 7/1982 | Kikumoto | 544/360 |
| 4,857,644 | 8/1989 | Abou-Gharbia | 544/295 |
| 4,910,302 | 3/1990 | Abou-Gharbia | 548/424 |

OTHER PUBLICATIONS

Br. J. Pharmacol. 90 273 (1987)—MDL 72832: A Potent, Selective and Stereospecific Ligand for 5-HT$_{1A}$ Receptors.
Kikumo et al, Chem. Abst. 98-53832c (1983).
Ota et al, Chem. Abst. 107-168629p (1987).
Otsuka Pharmaceutical Co. Ltd., Chem. Abst. 95-25121q (1981).
Franke et al, Chem. Abst. 96-199730y (1982).
Mitsubishi Chemical Industries Co. Ltd., Chem. Abst. 97-104233x (1982).
Agarwal et al, Chem. Abst. 98-53648x (1983).

*Primary Examiner*—Cecilia Shen
*Attorney, Agent, or Firm*—Richard K. Jackson

[57] ABSTRACT

There are disclosed compounds of the formula

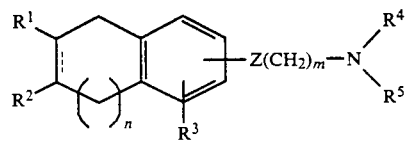

wherein
R$^1$ and R$^2$ are each, independently, hydrogen, alkyl, or phenyl, or R$^1$ and R$^2$ taken together represent —(CH$_2$)$_4$— or

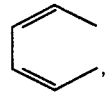

where the dotted line represents an optional double bond;
R$^3$ is hydrogen, alkyl, alkoxy, or halo;
Z is oxygen, or —N(R$^6$), where R$^6$ is hydrogen or alkyl;
m is 1–4;
n is 0–2;

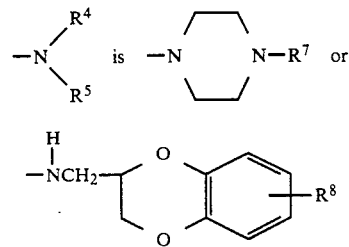

wherein
R$^7$ is unsubstituted or substituted phenyl, 2-pyridinyl, 2-pyrimidinyl, 2-pyrazinyl, 3-pyridazinyl, or diphenylmethyl, where the substituents are selected from the group of alkyl, alkoxy, halo, cyano, nitro and trifluoromethyl;
R$^8$ is hydrogen, hydroxy, cyano, alkyl, alkoxy, halo, or NHR$^9$ where R$^9$ is hydrogen, alkyl, phenyl, tolyl, xylyl, mesityl, methoxyphenyl, or halophenyl with the proviso when Z is oxygen, R$^7$ is other than phenyl or pyridyl;

or a pharmaceutically acceptable salt thereof, which by virtue of high affinity for the dopamine D-2 receptor and the serotonin 5-HT-$_{1A}$ receptor, are useful as antipsychotic and anxiolytic agents for the treatment of a variety of central nervous system disorders such as paranoia, schizophrenia, anxiety, sleep disorders, and related problems.

13 Claims, No Drawings

POLYCYCLIC PHENALKYL AMINES AS PSYCHOTROPIC AGENTS

BACKGROUND OF THE INVENTION

In addition to treatment of anxiety, 5-HT$_{1A}$ partial agonists are now being examined for their antidepressant potential. The therapeutic potential of the 5-HT$_{1A}$ agents in the treatment of multi-CNS disorders was recently extended to the development of compounds such as umespirone as antipsychotic-anxiolytic (Inter. Congress on Behavioral Pharmacology of 5-HT, page 49, Amsterdam, Netherland, 1987). Umespirone is described in German Patent No. 3529872.3 which discloses a series of 3-butyl-9,9-dimethyl diazabicycloalkylpiperazine tetranones as CNS agents.

Fozard et al., Br. J. Pharmacol. 90, 273P (1987) discloses 8-[4-(1,4-benzodioxan-2-ylmethylamino)butyl]-8-azaspiro[4,5]decane-7,9-dione as a stereospecific ligand for 5-HT$_{1A}$ receptors which differs from the present invention in the nature of the substituents attached to the 1,4-benzodioxan-2-ylmethylamino side chain.

The preparation of arylsulfonopiperazines have been disclosed in U.S. Pat. No. 4,857,644 as anti-inflammatory agents. The compounds in the present invention differ from the above-mentioned patent in the utility and nature of the substituents connecting the aryl ring to the piperazine side chain.

A series of piperazinylalkoxyindones were disclosed in U.S. Pat. No. 4,339,580 as anxiolytics. The compounds in the present invention are devoid of an oxygen bridging the piperazine side chain to the aryl ring when the piperazine ring is substituted with an aryl or pyridyl moiety. The above-mentioned feature is obligatory in U.S. Pat. No. 4,339,580.

U.S. Pat. No. 4,910,302 discloses a series of polycyclic imides containing a 1,4-benzodioxan-2-ylmethylamino side chain as psychotropic agents. The present invention is devoid of the polycyclic imide moiety.

DESCRIPTION OF THE INVENTION

In accordance with the invention, there is provided a group of antipsychoticanxiolytic agents of the formula:

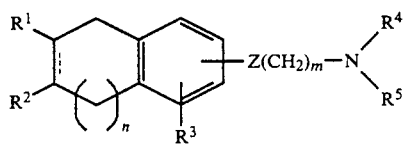

wherein
R$^1$ and R$^2$ are each, independently, hydrogen, alkyl of 1-6 carbon atoms, or phenyl, or R$^1$ and R$^2$ taken together represent —(CH$_2$)$_4$— or

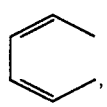

where the dotted line represents an optional double bond;
R$^3$ is hydrogen, alkyl of 1-6 carbon atoms, alkoxy of 1-6 carbon atoms, or halo;
Z is oxygen, or —N(R$^6$), where R$^6$ is hydrogen or alkyl of 1-6 carbon atoms;
m is 1-4;
n is 0-2;

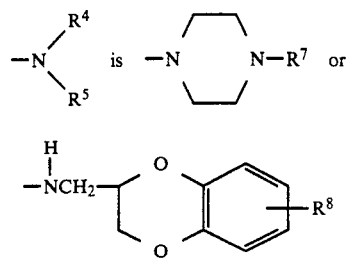

wherein
R$^7$ is unsubstituted or substituted phenyl, 2-pyridinyl, 2-pyrimidinyl,
2-pyrazinyl, 3-pyridazinyl, or diphenylmethyl, where the substituents are selected from the group of alkyl of 1-6 carbon atoms, alkoxy of 1-6 carbon atoms, halo, cyano, nitro and trifluoromethyl;
R$^8$ is hydrogen, hydroxy, cyano, alkyl of 1 to 3 carbon atoms, alkoxy of 1 to 3 carbon atoms, halo, or NHR$^9$ where R$^9$ is hydrogen, alkyl of 1-3 carbon atoms, phenyl, tolyl, xylyl, mesityl, methoxyphenyl, or halophenyl with the proviso when Z is oxygen, R$^7$ is other than phenyl or pyridyl;
or a pharmaceutically acceptable salt thereof.

Of these compounds, the preferred members are those in which Z is oxygen and —NR$^4$R$^5$ is 2-pyrimidinylpiperazinyl or diphenylmethylpiperazinyl and those in which Z is oxygen and —NR$^4$R$^5$ is 1,4-benzodioxan-2-yl-methylamino group.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

Compounds of this invention are prepared by conventional methods from starting materials that are available commercially or can be prepared by conventional methods disclosed in the literature. The compounds of this invention can be prepared by the following route:

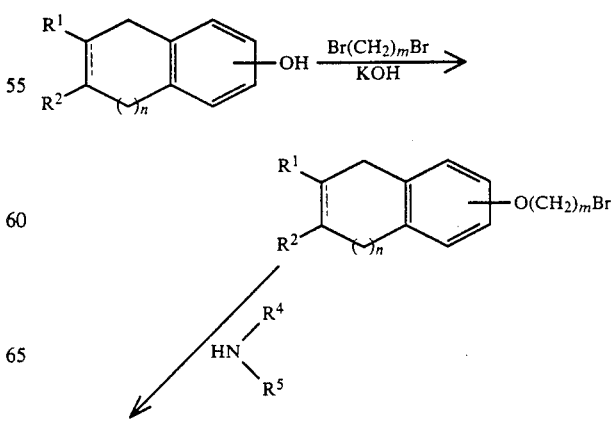

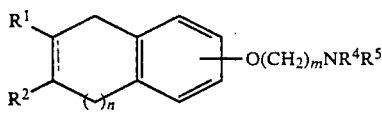

High affinity for the dopamine D-2 receptor was established by the standard experimental test procedure of Fields et al., Brain Res., 136, 578 (1977) and Yamamura et al., eds. Neutrotransmitter Receptor Binding, Raven Press, N.Y. (1978) wherein homogenized limbic brain tissue is incubated with $^3$H-spiroperidol and various concentrations of test compound, filtered and washed and shaken with Hydrofluor scintillation cocktail (National Diagnostics) and counted in a Packard 460 CD scintillation counter. The results of this testing with compounds representative of this invention is given below.

High affinity for the serotonin 5-HT$_{1A}$ receptor was established by testing the claimed compounds ability to displace [$^3$H]-8-OHDPAT (dipropylaminotetralin) from the 5-HT$_{1A}$ serotonin receptor following the procedure of Hall et al., J. Neurochem. 44, 1685 (1985). This procedure is employed to analogize this property of the claimed compounds with that of buspirone which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity (Vander Maclen et al., Eur. J. Pharmacol. 1986, 129 (1–2), 133–130.

The results of the two standard experimental test procedures described in the preceding two paragraphs was as follows:

| Compound | D-2 Binding (% Inhibition at 1 μM) | 5-HT$_{1A}$ Binding (% Inhibition at 1 μM) |
| --- | --- | --- |
| Example 1 | 85 | 91 |
| Example 2 |    | 43 |
| Example 3 | 82 | 48 |
| Example 4 | 97 | 92 |
| Example 5 | 100 | 76 |
| Example 6 | 95 | 99 |

The compounds of this invention possess high affinities for the dopamine D-2 receptor and the serotonin 5-HT$_{1A}$ receptor, and consequently they are useful as antipsychotic and anxiolytic agents for the treatment of a variety of central nervous system disorders such as paranoia, schizophrenia, anxiety, sleep disorders, and related problems.

The compounds may be administered neat or with a pharmaceutical carrier to a patient in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific anxiety disorder must be subjectively determined by the attending physician. The variables involved include the specific state of anxiety and the size, age and response pattern of the patient.

The following examples illustrate the production of representative compounds of this invention.

EXAMPLE 1

2-[4-[3-(2,3-Dihydro-1H-indan-5-yl)oxy]propyl]-1-piperazinyl]pyrimidine

To a stirred solution of 5-(3-bromopropoxy)indan (4.0 g, 0.015 mol) and 2-pyrimidinylpiperazine dihydrochloride (3.7 g, 0.015 mol) in 250 mL of DMF was added triethylamine (8.5 mL, 6.1 g, 0.06 mol). Stirring was continued overnight at 70° C., DMF was evaporated under reduced pressure, and the remaining residue was extracted with ethyl acetate (3×80 mL). The combined extracts were washed with water, dried over anhydrous Na$_2$SO$_4$ and evaporated under reduced pressure to afford 8.6 g of crude title compound which was purified by preparative HPLC to afford 2.7 g of pure free base which was converted to the dihydrochloride salt, mp 218°–220° C.

Anal. for $C_{20}H_{26}N_4O\cdot2HCl\cdot\frac{1}{2}H_2O$: Calcd: C, 57.14; H, 6.95; N, 13.33. Found: C, 56.72; H, 6.86; N, 13.21.

EXAMPLE 2

1-[4-[3-[(2,3-Dihydro-1H-indan-5-yl)oxy]propyl]-1-piperazinyl]bis(4-fluorophenyl)methane To a stirred solution of 5-(3-bromopropoxy)indan (3.5 g, 0.013 mol) and 1-bis(4-fluorophenyl)methylpiperazine (3.7 g, 0.01 mol) in 250 mL of DMF was added triethylamine (8.5 mL, 6.1 g, 0.06 mol). Stirring was continued overnight at 70° C., DMF was evaporated under reduced pressure, and the remaining residue was extracted with ethyl acetate (3×80 mL). The combined extracts were washed with water, dried over anhydrous $Na_2SO_4$ and evaporated under reduced pressure to afford crude title compound which was purified by preparative HPLC to afford 3 g of pure free base which was converted to the dihydrochloride salt, mp 208°-210° C.

Anal. for $C_{29}H_{32}F_2N_2O\cdot2HCl$: Calcd: C, 65.05; H, 6.36; N, 5.23, Cl, 13.27. Found: C, 64.74; H, 6.19; N, 5.14, Cl, 13.49.

EXAMPLE 3

2-Chloro-6-[4-[3-[(2,3-dihydro-1H-indan-4-yl)oxy]propyl]-1-piperazinyl]pyrazine

To a stirred solution of 5-(3-bromopropoxy)indan (3.5 g, 0.01 mol) and (6-chloro-2-pyrazinyl)piperazine (3 g, 0.015 mol) in 250 mL of DMF was added triethylamine (8.5 mL, 6.1 g, 0.06 mol). Stirring was continued overnight at 70° C., DMF was evaporated under reduced pressure, and the remaining residue was extracted with ethyl acetate (3×80 mL). The combined extracts were washed with water, dried over anhydrous $Na_2SO_4$ and evaporated under reduced pressure to afford the crude title compound which was purified by preparative HPLC to afford 3.0 g of free base which was converted to the hydrochloride, mp 237°-238° C.

Anal. for $C_{20}H_{25}ClN_4O\cdot HCl$: Calcd: C, 58.67; H, 6.35; N, 13.76, Cl, 17.38. Found: C, 58.25; H, 6.64; N, 13.69, Cl, 18.00.

EXAMPLE 4

N-[4-[(2,3-Dihydro-1H-indan-5-yl)oxy]butyl]-2,3-dihydro-1,4-benzodioxan-2-methanamine To a stirred solution of 5-(3-bromobutoxy)indan (0.98 g, 0.003 mol) and 1,4-benzodioxan-2-methane amine (0.60 g, 0.003 mol) in 50 mL of DMF was added triethylamine (1.5 mL, 1.1 g, 0.01 mol). Stirring was continued overnight at 70° C., DMF was evaporated under reduced pressure, and the remaining residue was extracted with methylene chloride (3×30 mL). The combined extracts were washed with water, dried over anhydrous $Na_2SO_4$ and evaporated under reduced pressure to afford 1.3 g of crude title compound which was purified by preparative HPLC to afford 0.3 g of pure free base which was converted to the hydrochloride, mp 150°-154° C.

Anal. for $C_{22}H_{27}NO_3\cdot HCl$: Calcd: C, 67.77; H, 6.98; N, 3.59. Found: C, 66.87; H, 7.13; N, 3.61.

EXAMPLE 5

N-[2-[(2,3-Dihydro-1H-indan-5-yl)oxy]ethyl]-2,3-dihydro-1,4-benzodioxan-2-methanamine To a stirred solution of 5-(3-bromoethoxy)indan (1.34 g, 0.005 mol) and 1,4-benzodioxan-2-methane amine (0.9 g, 0.005 mol) in 50 mL of DMF was added triethylamine (4.2 mL, 3.0 g, 0.03 mol). Stirring was continued overnight at 70° C., DMF was evaporated under reduced pressure, and the remaining residue was extracted with methylene chloride (3×50 mL). The combined extracts were washed with water, dried over anhydrous $Na_2SO_4$ and evaporated under reduced pressure to afford 1.8 g of crude title compound which was purified by preparative HPLC to afford 0.77 g of pure free base which was converted to the hydrochloride, mp 189°-194° C.

Anal. for $C_{20}H_{23}NO_3\cdot HCl$: Calcd: C, 66.38; H, 6.68; N, 3.87. Found: C, 66.37; H, 6.47; N, 4.07.

EXAMPLE 6

N-[3-[(2,3-Dihydro-1H-indan-5-yl)oxy]propyl]-2,3-dihydro-1,4-benzodioxan-2-methanamine To a stirred solution of 5-(3-bromopropoxy)indan (1.5 g, 0.01 mol) and 1,4-benzodioxan-2-methane amine (1 g, 0.01 mol) in 250 mL of DMF was added triethylamine (8.4 mL, 6.0 g, 0.06 mol). Stirring was continued overnight at 70° C., DMF was evaporated under reduced pressure, and the remaining residue was extracted with ethyl acetate (3×80 mL). The combined extracts were washed with water, dried over anhydrous $Na_2SO_4$ and evaporated under reduced pressure to afford 0.75 g of crude title compound which was purified by flash chromatography to afford 0.59 g of pure free base which was converted to the hydrochloride, mp 194°-195° C.

Anal. for $C_{21}H_{25}NO_3\cdot HCl$: Calcd: C, 67.28; H, 6.72; N, 3.74. Found: C, 66.82; H, 6.88; N, 3.76.

What is claimed is:

1. A compound having the formula

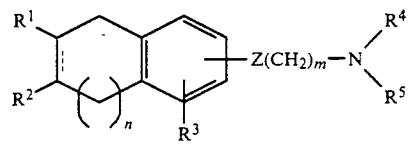

wherein $R^1$ and $R^2$ are each, independently, hydrogen, alkyl of 1-6 carbon atoms, or phenyl, or $R^1$ and $R^2$ taken together represent $-(CH_2)_4-$ or

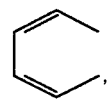

where the dotted line represents an optional double bond;

$R^3$ is hydrogen, alkyl of 1-6 carbon atoms, alkoxy of 1-6 carbon atoms, or halo;

Z is oxygen, or $-N(R^6)-$, where $R^6$ is hydrogen or alkyl of 1-6 carbon atoms;

m is 1-4;

n is 0-2;

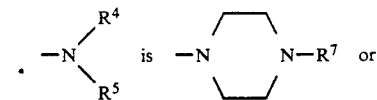

-continued

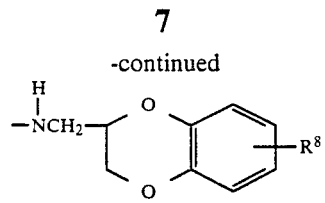

wherein
R[7] is unsubstituted or substituted phenyl, 2-pyridinyl, 2-pyrimidinyl, 2-pyrazinyl, 3-pyridazinyl, or diphenylmethyl, where the substituents are selected from the group of alkyl of 1-6 carbon atoms, alkoxy of 1-6 carbon atoms, halo, cyano, nitro and trifluoromethyl;

R[8] is hydrogen, hydroxy, cyano, alkyl of 1 to 3 carbon atoms, alkoxy of 1 to 3 carbon atoms, halo, or NHR[9] where R[9] is hydrogen, alkyl of 1-3 carbon atoms, phenyl, tolyl, xylyl, mesityl, methoxyphenyl, or halophenyl with the proviso when Z is oxygen, R[7] is other than substituted or unsubstituted phenyl, or substituted or unsubstituted pyridyl; or a pharmaceutically acceptable salt thereof.

2. A compound of claim 1 wherein Z is oxygen and NR[4]R[5] is

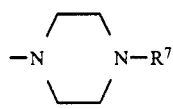

or a pharmaceutically acceptable salt thereof.

3. A compound of claim 1 wherein Z is oxygen and NR[4]R[5] is

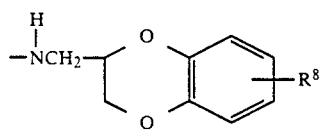

or a pharmaceutically acceptable salt thereof.

4. A compound of claim 1 which is 2-[4-[3-(2,3-dihydro-1H-indan-5-yl)oxy]propyl]-1-piperazinyl]pyrimidine or a pharmaceutically acceptable salt thereof.

5. A compound of claim 1 which is 1-[4-[3-[(2,3-dihydro-1H-indan-4-yl)oxy]propyl]-1-piperazino]bis(4-fluorophenyl)methane or a pharmaceutically acceptable salt thereof.

6. A compound of claim 1 which is 2-chloro-6-[4-[3-[(2,3-dihydro-1H-indan-4-yl)oxy]propyl]-1-piperazino]-pyrazine or a pharmaceutically acceptable salt thereof.

7. A compound of claim 1 which is N-[4-[(2,3-dihydro-1H-indan-5-yl)oxy]butyl]-2,3-dihydro-1,4-benzodioxan-2-methanamine or a pharmaceutically acceptable salt thereof.

8. A compound of claim 1 which is N-[2-[(2,3-dihydro-1H-indan-5-yloxy]ethyl]-2,3-dihydro-1,4-benzodioxan-2-methanamine or a pharmaceutically acceptable salt thereof.

9. A compound of claim 1 which is N-[3-[(2,3-dihydro-1H-indan-5-yl)oxy]propyl]-2,3-dihydro-1,4-benzodioxan-2-methanamine.

10. A method of treating a central nervous system disorder in a mammal in need thereof which comprises administering an antipsychotic or anxiolytic amount of a compound having the formula

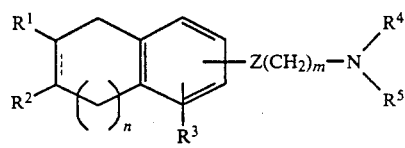

wherein
R[1] and R[2] are each, independently, hydrogen, alkyl of 1-6 carbon atoms or phenyl, or R[1] and R[2] taken together represent —(CH$_2$)$_4$— or

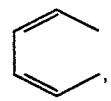

where the dotted line represents an optional double bond;

R[3] is hydrogen, alkyl of 1-6 carbon atoms, alkoxy of 1-6 carbon atoms, or halo;

Z is oxygen, or —N(R[6]), where R[6] is hydrogen or alkyl of 1-6 carbon atoms;

m is 1-4;

n is 0-2;

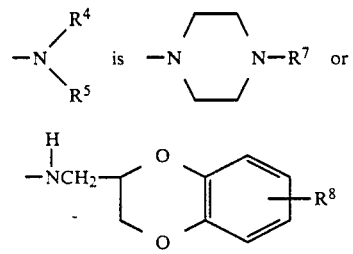

wherein
R[7] is unsubstituted or substituted phenyl, 2-pyridinyl, 2-pyrimidinyl, 2-pyrazinyl, 3-pyridazinyl, or diphenylmethyl, where the substituents are selected from the group of alkyl of 1-6 carbon atoms, alkoxy of 1-6 carbon atoms, halo, cyano, nitro and trifluoromethyl;

R[8] is hydrogen, hydroxy, cyano, alkyl of 1 to 3 carbon atoms, alkoxy of 1 to 3 carbon atoms, halo, or NHR[9] where R[9] is hydrogen alkyl of 1-3 carbon atoms, phenyl, tolyl, xylyl, mesityl, methoxyphenyl, or halophenyl with the proviso when Z is oxygen, R[7] is other than substituted or unsubstituted phenyl, or substituted or unsubstituted pyridyl; or a pharmaceutically acceptable salt thereof.

11. A pharmaceutical composition comprising an antipsychotic or anxiolytic amount of a compound of claim 1 or a pharmaceutically acceptable salt thereof and a pharmaceutically acceptable carrier.

12. A composition as claimed in claim 11, in unit dosage form.

13. A compound of claim 1 wherein Z is oxygen and —NR[4]R[5] is a 2-pyrimidinylpiperazinyl, diphenylmethylpiperazinyl, or 1,4-benzodioxan-2-yl-methylamino group or a pharmaceutically acceptable salt thereof.

* * * * *